United States Patent [19]
Brown

[11] Patent Number: 4,813,431
[45] Date of Patent: Mar. 21, 1989

[54] INTRAPULMONARY PRESSURE MONITORING SYSTEM

[76] Inventor: David Brown, 12 Hartwood Ct., Clifton Park, N.Y. 12065

[21] Appl. No.: 76,156

[22] Filed: Jul. 22, 1987

[51] Int. Cl.⁴ .............................................. A61B 5/00
[52] U.S. Cl. ................................ 128/748; 128/207.15
[58] Field of Search ...... 128/748, 780, 207.14–207.17, 128/673–675; 604/96–103

[56] References Cited

U.S. PATENT DOCUMENTS

| | | | |
|---|---|---|---|
| 3,893,451 | 7/1975 | Durand et al. | 128/673 |
| 4,214,593 | 7/1980 | Imbruce et al. | 128/748 |
| 4,252,131 | 2/1981 | Hon et al. | 128/673 X |
| 4,387,711 | 6/1983 | Merry | 604/96 X |
| 4,484,585 | 11/1984 | Baier | 128/748 |
| 4,502,490 | 3/1985 | Evans et al. | 128/780 |
| 4,621,646 | 11/1986 | Bryant | 128/692 |
| 4,672,974 | 6/1987 | Lee | 128/748 X |

Primary Examiner—Kyle L. Howell
Assistant Examiner—Angela D. Sykes
Attorney, Agent, or Firm—Schmeiser, Morelle & Watts

[57] ABSTRACT

A pressure sensing device hydraulically coupled with a transducer comprising a closed hydraulic system incorporated within an endotracheal tube to monitor intrapulmonary pressure. The tube employs an hydraulic system for conveying pressure data from a distal sensor, on the tube, to a transducer. The sensor and transducer are connected by a liquid-filled lumen. Use of an hydraulic conduit avoids the errors of gas-filled systems because liquids, such as the water used in this system, are incompressible.

9 Claims, 2 Drawing Sheets

INTRAPULMONARY PRESSURE MONITORING SYSTEM

FIELD OF THE INVENTION

This invention relates to measurement of intrapulmonary pressure within a lung by use of an endotracheal tube having a pressure sensor and signal conduit that communicate with an hydraulic pressure transducer.

BACKGROUND OF THE INVENTION

The present invention has been developed to lessen the incidence of bronchopulmonary dysplasia (BPD, a chronic lung problem found in premature infants) caused by mechanical ventilation. Although not conclusively proven, pulmonary barotrauma due to mechanical ventilation is thought to be an important etiological factor in BPD.

The present invention allows accurate determination of increases in pulmonary dynamic compliance. These increases permit decreases in the mean airway pressure to be made during mechanical ventilation. Decreasing mechanical ventilation pressure reduces the incidence and severity of pulmonary barotrauma.

An exhaustive search of the prior art disclosed several patents which pertained to the construction or production of devices that utilize an hydraulic medium with an endotracheal tube. Issued to Baum in 1985, U.S. Pat. No. 4,535,766 discloses a method and apparatus for monitoring a respirator in use with an endotracheal tube. The pressure of the respiratory gas source is controlled through a pneumatic link with a measuring tube which terminates at or near the distal end of the endotracheal tube. Baum also teaches an open hydraulic system and indicates that water (the fluid) emitted by a jet nozzle serves to humidify the respiratory gas. The invention's purpose in using a liquid fluid, therefore, is to humidify and not to monitor intrapulmonary pressure. This is a state of the art employment of an hydraulic fillen lumen within a standard endotracheal tube.

Issued to Jackson, U.S. Pat. No. 3,854,484, discloses a closed hydraulic system within close proximity of the endotracheal tube. The Jackson device, instead of using air to fill the occlusive cuff of an endotracheal tube, uses a liquid medium. Jackson discloses no other purpose for the closed hydraulic system than sealing the area between the endotracheal tube and esophogeal wall.

The present methods of dynamic monitoring of intrapulmonary pressures include central venous pressure, transpulmonary (esophageal) and distal pneumatic catheterization. These three modes of monitoring suffer limited accuracy due to: (1) indirect measurement of pneumobarometic pressure, because the target pressure area is beyond the placement of the intratracheal artificial airway; (2) the influence of the non-airway artifact on the intrapulmonary pressure; and (3) external (ambient) air pressure influence upon an open transducing system.

It is therefore the object of this invention to provide a new intrapulmonary monitoring device which does not rely upon these three modes and therefore avoids their disadvantageous aspects. This is accomplished by: (1) locating the sensor proximate the pulmonary region to be measured; (2) positioning the sensor near the exterior, distal end of the endotracheal tube, thus eliminating the artifact effect of turbulent air flow; and (3) utilizing a closed hydraulic sensor-transmitter system, eliminating the problems relating to an open system, namely, avoiding errors due to air compression by using an incompressible fluid.

SUMMARY OF THE INVENTION

The present invention contemplates an intrapulmonary pressure monitoring system which uses a standard endotracheal tube (with occlusive restriction means) to sense, i.e., detect pneumobarometric pressure near the distal end of the tube which is located proximate the lung. Next, it invariably transmits these data to a transducing means. The transducing means will then convert the accurately sensed and transmitted pneumobarometic pressure data to a readable form.

A standard endotracheal tube is modified to satisfy the objects of this invention. Means for sensing and transmitting (hydraulically) the pneumobarometric pressure consists of a liquid-filled, closed lumen placed coextensive to and inside the outer surface of the endotracheal tube; the distal end of the lumen terminates with and is sealed by a resilient diaphragm, while its proximal end terminates with and is sealed by a pressure transducer. The diaphragm is placed near the distal end of the endotracheal tube, and the pressure transducer placed near the proximal end of the tube.

The hydraulic pressure transducer converts the sensed pressure to electrical signals for further data analysis. It is necessary to seal off the lungs and airway from ambient environment. To this end, ordinary sealing is provided by the standard occlusive cuff which may be either air or liquid filled (cf. Background of the Invention).

The accompanying drawings illustrate preferred embodiments of the invention, and together with the description, serve to explain the principles of the invention. The inventor herein uses the term "chamber" in its normal sense, and the term "lumen" interchangeably and meaning a tube-like conduit. Synonymously, "conduit" may also be used.

DETAILED DESCRIPTION OF THE DRAWINGS

Figure 1:
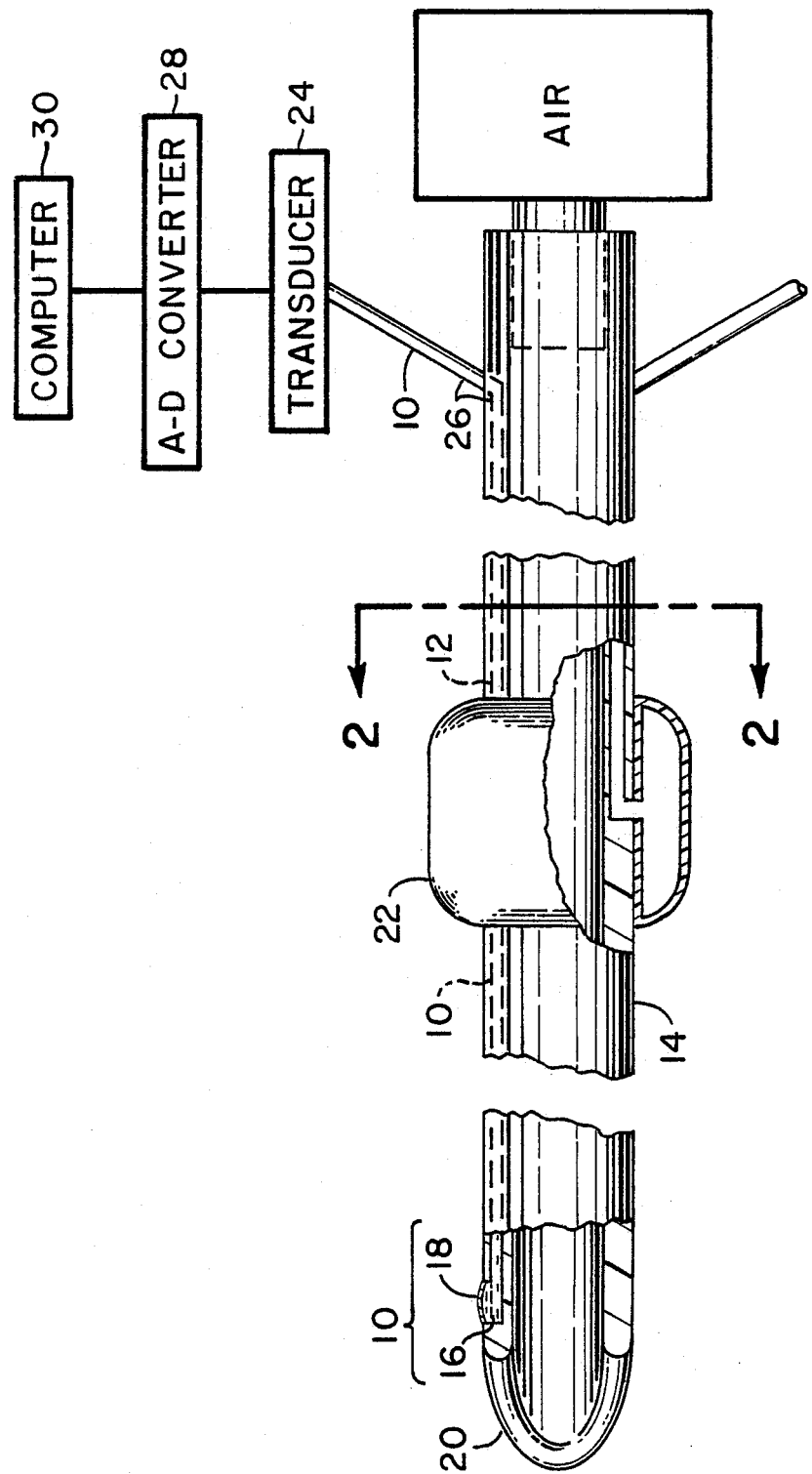
FIG. 1 is a cross-sectional view of the preferred embodiment emplaced in a LaConte tube.

Referring more particulary to FIG. 1, there is a depiction of a LaConte tube 10 modified with the invention. The liquid-filled lumen or chamber 12 is placed coextensive to and inside the outer surface of the LaConte (endotracheal) tube 14. The lumen's distal and terminating end 16 is sealed with a resilient diaphragm 18 which herein is depicted as a cuff and which lies exterior to the outer wall 14 of the tube and between the distal end of the tube 20 and the occlusive cuff 22. The occlusive cuff is a standard element of the LaConte device and most endotrachael tubes.

The proximal end 26 of the liquid filled lumen 12 is sealed by an hydraulic pressure transducer 24. An analog digital converter 28 receives the electrical signals from the transducer 24. After conversion, a computer 30 compiles the data to render it in readable form, e.g., in millimeters of mercury, and calculates compliance.

Figure 2:
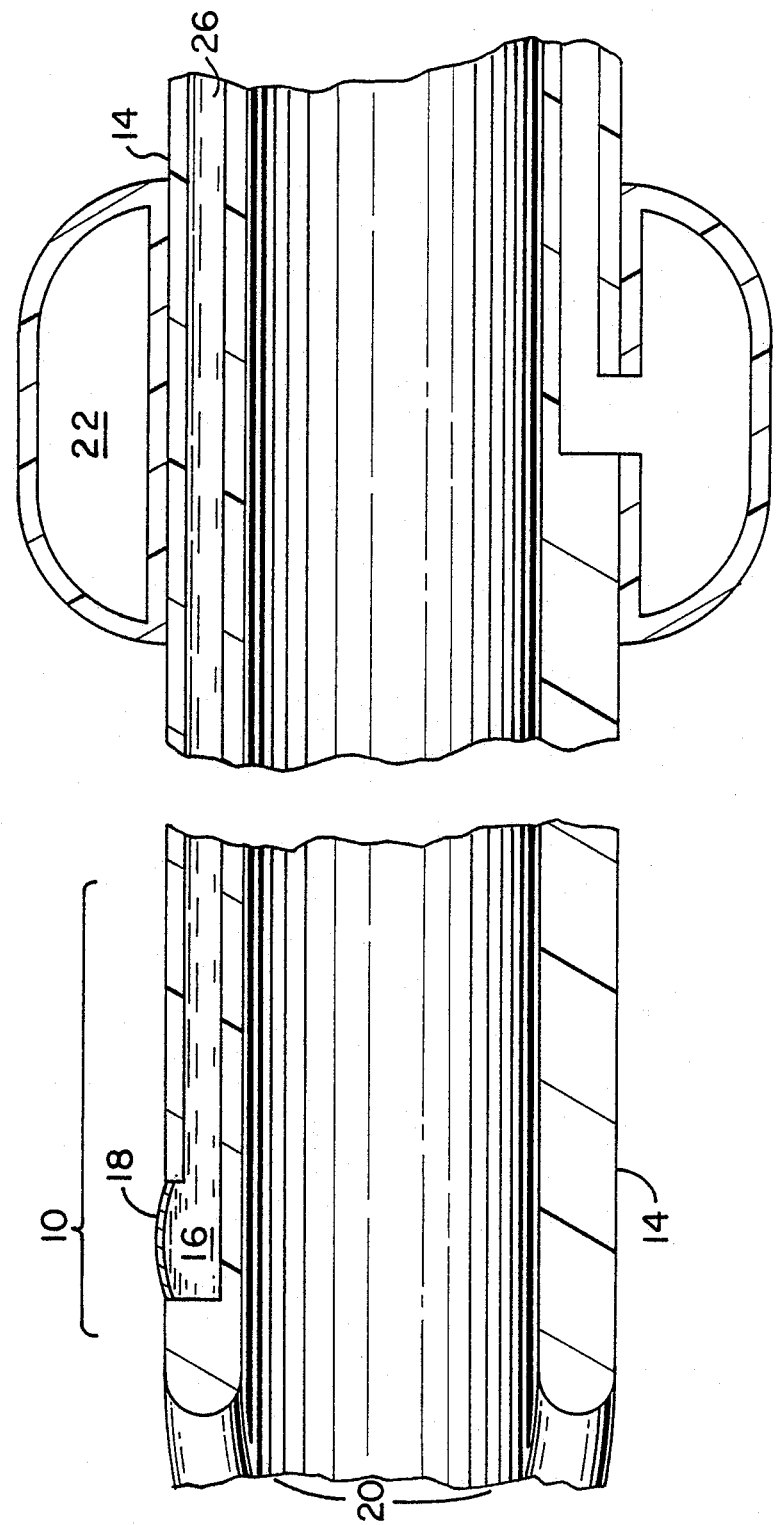
FIG. 2 is a cross-sectional view of the distal end of the invention.

In FIG. 2, an enlarged and more detailed view of the distal end 16 of the hydraulic system is represented. The liquid-filled chamber or lumen 12 lies inside the wall of the LaConte tube 14. The resilient sensor membrane 18 lies toroidially, in this particular version, about the tube's outer wall and communicates with the interior of the lumen 12.

Unlike the occlusive cuff, which must be of essentially toroidial shape, in order to interpose an airway blockage, those skilled in this art will recognize that no distinct shape must be accorded the membrane or diaphram-sensor 18. In many applications, for example in neonatals or very small children, the only physical condition demanded of the sensor, in the instant invention, is that it seal the distal end 16 of the chamber or lumen 12 from the external environment (cf. FIG. 1). The lumen is filled completely with a liquid medium (the inventor prefers pure water with salinity adjusted for various physiological requirements). Thus, the sensor 18 may be a diaphragm-like or membranous "button" contiguous with the terminus 16 of lumen 12, and covering it sufficiently to seal off the lumen, thereby establishing the closed hydraulic system that is the essence of the invention.

What is claimed:

1. An apparatus for measuring air pressure within the lung comprising:
    a standard endotracheal tube with occlusive cuff to seal the air passageway between the tube surface and tracheal surface when the tube is inserted into the trachea;
    means for sensing and hydraulically transmitting to a transducing means the pneumobarometric pressure near the distal end of said tube after said end is emplaced within the pulmonary region and where said means for sensing and transmitting comprises a liquid-filled lumen coextensive to and inside the outer surface of said tube, said lumen's distal end terminating with and sealed by a resilient diaphragm and its proximal end terminating with and sealed by a pressure transducer, said diaphragm proximate the distal end of said tube at its outer periphery, said diaphragm being essentially contiguous with said tube's outer surface, the liquid of said liquid-filled lumen thus isolated from the air within said lung; and
    liquid-phase transducing means for converting the sensed pneumobarometric pressure to a usable data form.

2. The invention of claim 1 wherein said transducing means is an hydraulic pressure transducer which converts the sensed pressure to electrical signals for further processing.

3. An hydraulic mechanism for measuring pressure comprising:
    an endotracheal tube, having proximal and distal ends, for inserting the distal end thereof into the interior of a body organ and possessing a coextensive integral interior wall chamber, said chamber having a proximal opening therefrom and a distal opening which communicates with the outer periphery of said tube near the distal end thereof and;
    a liquid pressure transducer connected to and sealing said chamber near said proximal opening;
    a resilient membrane covering and sealing said distal opening, isolating the interior of said chamber, said membrane located proximate said distal end and being essentially contiguous to said tube's outer periphery, and
    a liquid to completely fill the closed volume defined by said transducer, said chamber and said membrane, said liquid to be completely isolated from any fluid within said organ, whereby a force exerted upon the surface of said membrane will be transmitted hydraulically and precisely throughout said volume and be rendered readable by the operation of said transducer.

4. The invention of claim 3 wherein said wall chamber further comprises a lumen which extends from the proximal end of said tube and passes co-linearly along and through a standard, cuffed endotracheal tube to exit at said tube's outer surface near its distal end between said distal end and said cuff.

5. The invention of claim 4 wherein said resilient membrane further comprises an annular cuff resembling the standard toroidial occlusive cuff, said cuff communicating with said lumen.

6. The invention of claim 4 wherein said liquid is sterile water.

7. In an apparatus composed of an endotracheal tube having proximal and distal ends and an outer periphery, an improved pneumopressure measurement system comprising the combination of:
    a liquid-filled lumen having a proximal end and a distal end and placed coextensively within said tube;
    a resilient, membranous diaphragm which seals said lumen distal end, said diaphragm being positioned proximate to said tube's distal end and residing contiguous to said tube's outer periphery; and
    a pressure transducer which seals said lumen proximal end so that in combination with said diaphragm, the liquid filling of said lumen is completely contained and isolated from conditions external to said lumen, whereby when said lumen is used in combined operation with said endotracheal tube and, with said tube distal end placed within the site of pneumopressure measurement, the pressure sensed on said diaphragm is hydraulically transmitted to said transducer which converts pressure data to a readable form.

8. The invention of claim 7 wherein the liquid within said lumen is sterile water.

9. A method for measuring lung compliance comprising the steps of:
    sensing pneumopressure by inserting into the lung through the trachea a liquid filled lumen that is sealed at the distal end by a membranous diaphragm and at the proximal end by an hydraulic transducer so that the liquid of said lumen is isolated from lung fluid;
    transmitting the pneumopressure sensed within the lung by conveying the pressure sensed on said diaphragm through the liquid of said lumen to the hydraulic transducer; and
    transducing pneumopressure that has been transmitted to said transducing means to usable, readable information.

* * * * *